(12) United States Patent
McKinnon et al.

(10) Patent No.: US 8,062,266 B2
(45) Date of Patent: Nov. 22, 2011

(54) VASCULAR ACCESS DEVICE INCLUDING A TEAR-RESISTANT SEPTUM

(75) Inventors: Austin Jason McKinnon, Herriman, UT (US); Alexy T. Yessayan, South Jordan, UT (US); Lantao Guo, Draper, UT (US); David Ou-Yang, Woodbury, MN (US); Yongming Liu, Basking Ridge, NJ (US); Kelly D. Christensen, Centerville, UT (US); Weston F. Harding, Lehi, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 344 days.

(21) Appl. No.: 11/866,822

(22) Filed: Oct. 3, 2007

(65) Prior Publication Data

US 2008/0132832 A1 Jun. 5, 2008

Related U.S. Application Data

(60) Provisional application No. 60/829,092, filed on Oct. 11, 2006.

(51) Int. Cl.
*A61M 5/24* (2006.01)
*A61M 5/28* (2006.01)
*A61M 5/178* (2006.01)

(52) U.S. Cl. .................... 604/201; 604/167.02
(58) Field of Classification Search ............... 604/93.01, 604/167.02, 201–206
See application file for complete search history.

(56) References Cited

U.S. PATENT DOCUMENTS

| | | | |
|---|---|---|---|
| 4,765,588 A | 8/1988 | Atkinson | |
| 5,251,873 A | 10/1993 | Atkinson et al. | |
| 5,269,771 A | 12/1993 | Thomas et al. | |
| 5,295,657 A | 3/1994 | Atkinson | |
| 5,295,658 A | 3/1994 | Atkinson et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,540,661 A * | 7/1996 | Tomisaka et al. | ............. 604/265 |
| 5,549,651 A | 8/1996 | Lynn | |
| 5,957,898 A | 9/1999 | Jepson et al. | |
| 6,171,287 B1 | 1/2001 | Lynn et al. | |
| 6,261,282 B1 | 7/2001 | Jepson et al. | |
| RE37,357 E | 9/2001 | Lynn | |
| 6,344,033 B1 | 2/2002 | Jepson et al. | |
| 6,595,964 B2 | 7/2003 | Finley et al. | |
| 6,651,956 B2 | 11/2003 | Miller | |
| 6,669,681 B2 | 12/2003 | Jepson et al. | |
| 6,866,656 B2 | 3/2005 | Tingey et al. | |
| 6,908,459 B2 | 6/2005 | Harding et al. | |
| 2002/0193752 A1 | 12/2002 | Lynn | |
| 2003/0036735 A1 | 2/2003 | Jepson et al. | |
| 2005/0256500 A1 | 11/2005 | Fujii | |

FOREIGN PATENT DOCUMENTS

WO WO 91/05581 5/1991
* cited by examiner

*Primary Examiner* — Nicholas D Lucchesi
*Assistant Examiner* — Rebecca E Eisenberg
(74) *Attorney, Agent, or Firm* — Mony R. Ghose; Kirton & McConkie (57) ABSTRACT

A vascular access device within an external environment may include a body and a septum at least partially housed within the body. Septum may at least substantially seal a lumen extending through the body. The septum may further include at least a first and a second material. At least one of the materials of the septum may be selected or adapted to resist tearing of the septum.

20 Claims, 7 Drawing Sheets

VASCULAR ACCESS DEVICE INCLUDING A TEAR-RESISTANT SEPTUM

RELATED APPLICATIONS

This application claims the benefit of U.S. Provisional Application No. 60/829,092, filed Oct. 11, 2006, entitled VASCULAR ACCESS DEVICES INCLUDING A TEAR-RESISTANT SEPTUM, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

Vascular access devices commonly include a Luer adapter, or other connector or adapter, to which other medical devices may be attached. For example, an IV (intravenous) administration set may be attached to a vascular access device to provide a fluid conduit for the continuous infusion of fluids and pharmaceuticals from an intravenous (IV) bag. A variety of medical devices may cooperate with vascular access devices to provide selective, temporary, or long-term access to the vascular system of a patient. A vascular access device may include a body having a lumen therethrough and a septum for selectively closing the lumen. The septum may be opened with a blunt cannula, a male Luer of a medical device, or other suitable medical device.

Vascular access devices provide many significant benefits to patients and medical practitioners. A vascular access device is most beneficial to patients when the septum forms a proper seal between the accessed vascular system and the outside or external environment. In an ideal vascular access device, the septum would continuously seal the patient's vascular system, which may include external vascular equipment intentionally coupled to the patient's internal vascular system by a medical practitioner, from the external environment.

As with most systems, one of the biggest challenges to the proper function of the vascular access device is when there is a change in the system, such as when different medical devices are connected or disconnected from the vascular access device. If the seal against the external environment is broken during the connection or disconnection of a medical device, there is the possibility of infection being introduced into the patient's vascular system. Additionally, if a pressure difference is created across the vascular access device, there becomes the possibility that blood will be drawn up the catheter system and possibly into the vascular access device or beyond. Alternatively, a pressure difference across the vascular access device may make it more difficult to couple other medical devices to the vascular access device.

As introduced above, vascular access devices are often coupled with a blunted cannula, such as the tip of a syringe, with a male Luer connector, or with other medical devices. These medical devices may be coupled to the vascular access devices by pressing a portion of the medical device into a slit or passage in the septum. Some medical devices are coupled to the vascular access device through a twisting motion by which the body or other portion of the medical device is coupled to the body of the vascular access device and by which a portion of the medical device is disposed in the slit or passage of the septum. Other methods of coupling the vascular access device to one or more medical devices may be used as well.

Regardless of the methods used to couple medical devices to the vascular access device, repeated transitions of the septum between open and closed configurations applies stress to the septum. In some experiences the septum has been seen to tear, either slightly or more significantly, at the edges of the slit that allows other devices to access the internal vascular system through the lumen of the body. In previous vascular access devices, two common tear patterns have been observed: radial tearing and circumferential tearing. Depending on the nature of the tear, the impacts of the tear may include a decrease in the quality of the seal formed by the septum or pieces or particles of the septum breaking free from the remainder of the septum. In any event, a septum that is modified from the manufacturer's intended and safety-tested design is not preferred for a number of reasons. The present disclosure is directed to vascular access devices, and methods of manufacturing vascular access devices, that include a tear-resistant septum.

BRIEF SUMMARY OF THE INVENTION

A vascular access device may include a body and a septum. The body may define a lumen or passage extending through the body. The septum may be at least partially disposed in the body to at least substantially seal the lumen extending through the body. Additionally, the septum may include a slit adapted to provide selective passage through the septum. The septum may comprise at least a first and a second material with at least one of the materials being selected or configured to resist tearing of the septum.

The septum may be variously configured to resist tearing. As one example, the septum may include a longitudinal axis and the slit in the septum may have a slit width between a slit first end and a slit second end with the slit width extending orthogonally to the longitudinal axis. A saddle may include at least one slit stop disposed substantially adjacent to one or more of the slit first and second ends.

As another example, which may be combined with the other examples described herein, the septum of the vascular access device may include a second material that is a lubricating material. The lubricating material may be disposed on the exterior surface of the septum and may additionally or alternatively be disposed within the slit of the septum. For some applications of the present disclosure it may be desirable to include a septum of multiple materials, such as a first material for the majority of the septum, a second material to form slit stops, and a third material to provide a lubricating coating. Other such combinations of the principles and features disclosed herein are within the scope of the present disclosure whether specifically described or whether merely apparent from the disclosure.

In yet another example of the principles in the present disclosure, vascular access devices may include a septum comprising an elastomeric material. The elastomeric material, whether considered a second material or third or fourth material according to the various combinations possible within the scope of the present disclosure, may be disposed in operative association with the slit to provide selective expansion and contraction of the passage through the septum. For example, an elastomeric material may surround the slit provided in the septum to allow expansion of the preformed slit to avoid tearing.

Vascular access devices may be manufactured in any suitable manner. One exemplary method of manufacturing vascular access devices that include a tear-resistant septum may include providing a body having a first body end region and a second body end region and defining a lumen extending through the body. Additionally, the method may include providing a septum including a first septum end region and a second septum end region and having a slit extending from the first septum end region to the second septum end region. The provided septum comprises at least a first and a second material. Finally, the method may include disposing at least a portion of the septum in the body to at least substantially seal the passage extending through the body. In providing a septum comprising at least a first and a second material, at least one of the materials may be selected or configured to resist tearing.

Additionally or alternatively, providing a septum may comprise forming at least one slit stop disposed at least substantially adjacent to at least one of a slit first end and a slit second end. Similarly, providing a septum may include disposing a lubricating second material in operative association with the slit. In some implementations, a second material selected to resist tearing may be added to or incorporated into the septum after the septum is disposed in the body. In yet another exemplary implementation of the present methods, the step of providing a septum may include incorporating an elastomeric material into the septum, such as surrounding the slit, to provide selective expansion and contraction of the passage through the septum.

Vascular access devices according to the present disclosure may additionally or alternatively include a body means for selective coupling to a vascular system of a patient and to at least one additional medical device. The body means may have a passage extending therethrough to provide access to the patient's vascular system. The vascular access device may also include a sealing means including a slit for selectively and at least substantially sealing the passage through the body. Additionally, the vascular access device may include means for discouraging tearing of the sealing means adjacent the slit. In some implementations, the means for discouraging tearing may include a lubricating means disposed adjacent to at least a portion of the slit. Additionally or alternatively, the means for discouraging tearing may include a barrier means disposed adjacent to at least a portion of the slit. Additionally or alternatively, the means for discouraging tearing may include an expansive means disposed adjacent to at least a portion of the slit.

These and other features and advantages of the present disclosure may be incorporated into vascular access devices and will become more fully apparent from the following description and appended claims, or may be learned by the practice and implementation of the present disclosure. As described above, the present disclosure does not require that all of the features described herein be incorporated into every embodiment nor is it required that certain features be used exclusive of other features. Vascular access devices within the scope of the present disclosure may include one or more combinations of the features described herein.

BRIEF DESCRIPTION OF THE SEVERAL VIEWS OF THE DRAWINGS

In order that the above-recited and other features and advantages of the disclosure may be readily understood, a more particular description is provide below with reference to the appended drawings. These drawings depict only exemplary embodiments of vascular access devices according to the present disclosure and are not therefore to be considered to limit the scope of the disclosure.

DETAILED DESCRIPTION OF THE INVENTION

It will be readily understood that the components of the present disclosure, as generally described and illustrated in the figures herein, could be arranged and designed in a wide variety of different configurations. Thus, the following more detailed description, as represented in the figures, is not intended to limit the scope of the disclosure, but is merely a representative of exemplary combinations of the components.

Figure 1:
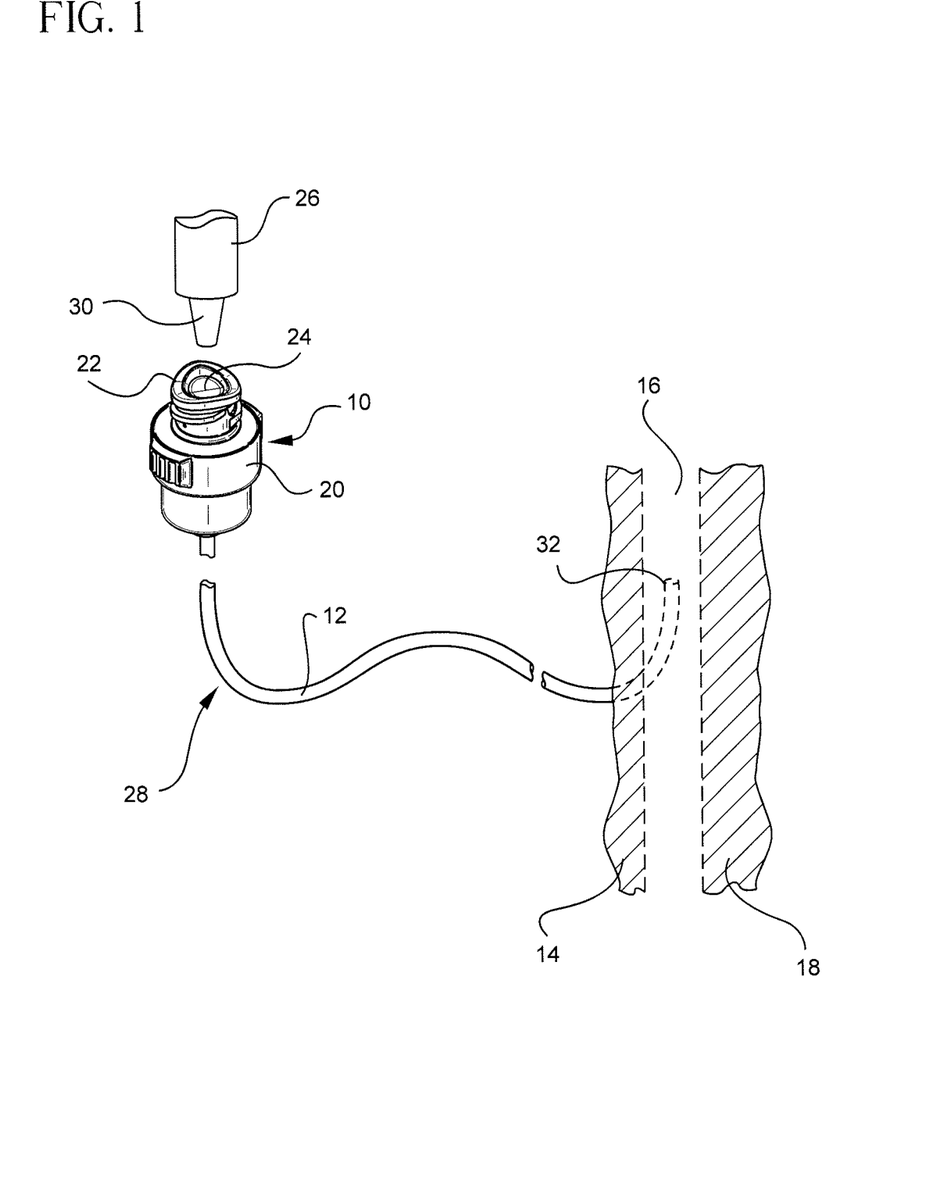
FIG. 1 is a perspective view of an extravascular system connected to the vascular system of a patient.

Referring now to FIG. 1, a vascular access device 10 is used to introduce a substance via a catheter 12 across the skin 14 and into a blood vessel 16 of a patient 18. The vascular access device 10 includes a body 20 with a lumen and a septum 22 placed within the lumen. The vascular access device 10, including the body 20 and the septum 22, will be more thoroughly described with reference to the remaining figures where particular features are better illustrated. As shown in FIG. 1, the septum 22 has a slit 24 through which a separate extravascular device 26, such as a syringe, may introduce a substance into the vascular access device 10. A syringe is one exemplary separate device 26. Other suitable extravascular devices may include additional vascular access devices, IV administration sets, or other common or yet to be developed medical devices.

The device 10 and all structures used in combination therewith may form a larger extravascular system 28. As part of operating the extravascular system 28, a tip 30 of the separate device 26 may be inserted into the vascular access device 10 through the slit 24 of the septum 22. The tip 30 penetrates the device 10 separating at least portions of the two opposing slit surfaces of the septum 22. The septum 22 and the slit 24 may be configured to seal, or at least substantially seal, around the tip 30 as it is inserted into the vascular access device 10. Accordingly, the surfaces near the slit ends may not be separated until the tip 30 is sufficiently inserted into vascular access device 10. The tip 30 serves to open the slit 24 to allow fluid to pass through the device 10, into the catheter 12, and out the end 32 of the catheter when the device is in use.

Figure 2:
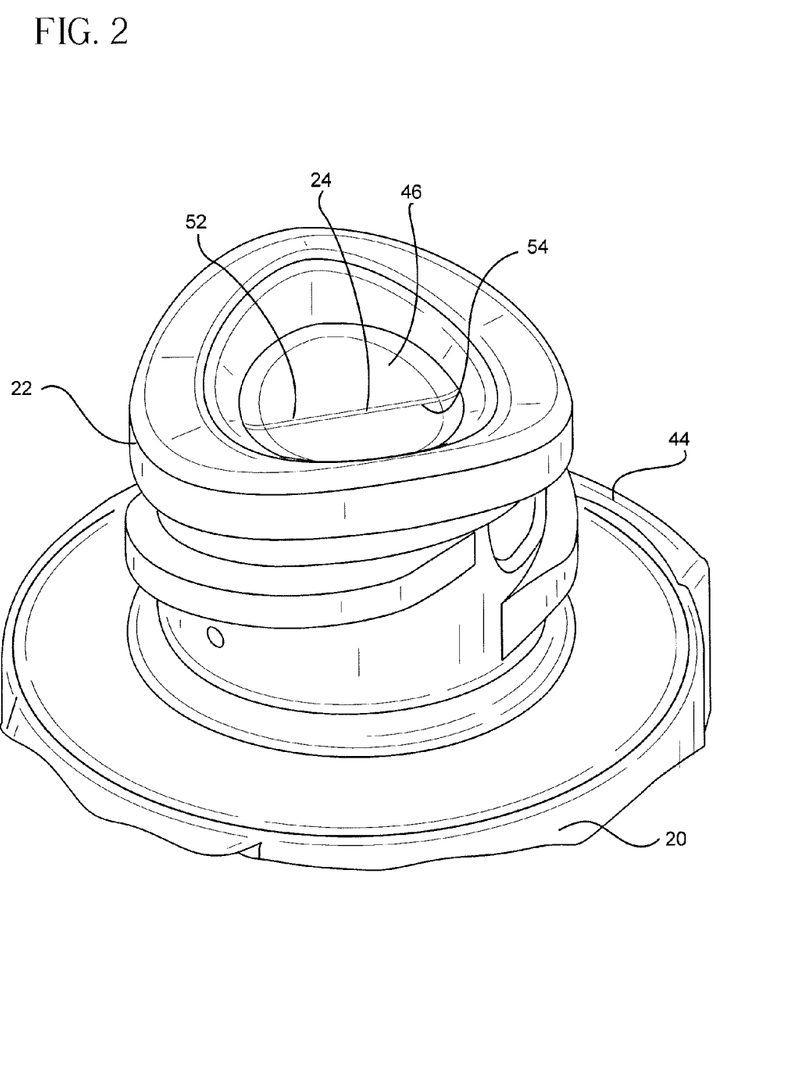
FIG. 2 is a perspective top view of a vascular access device.
Figure 3:
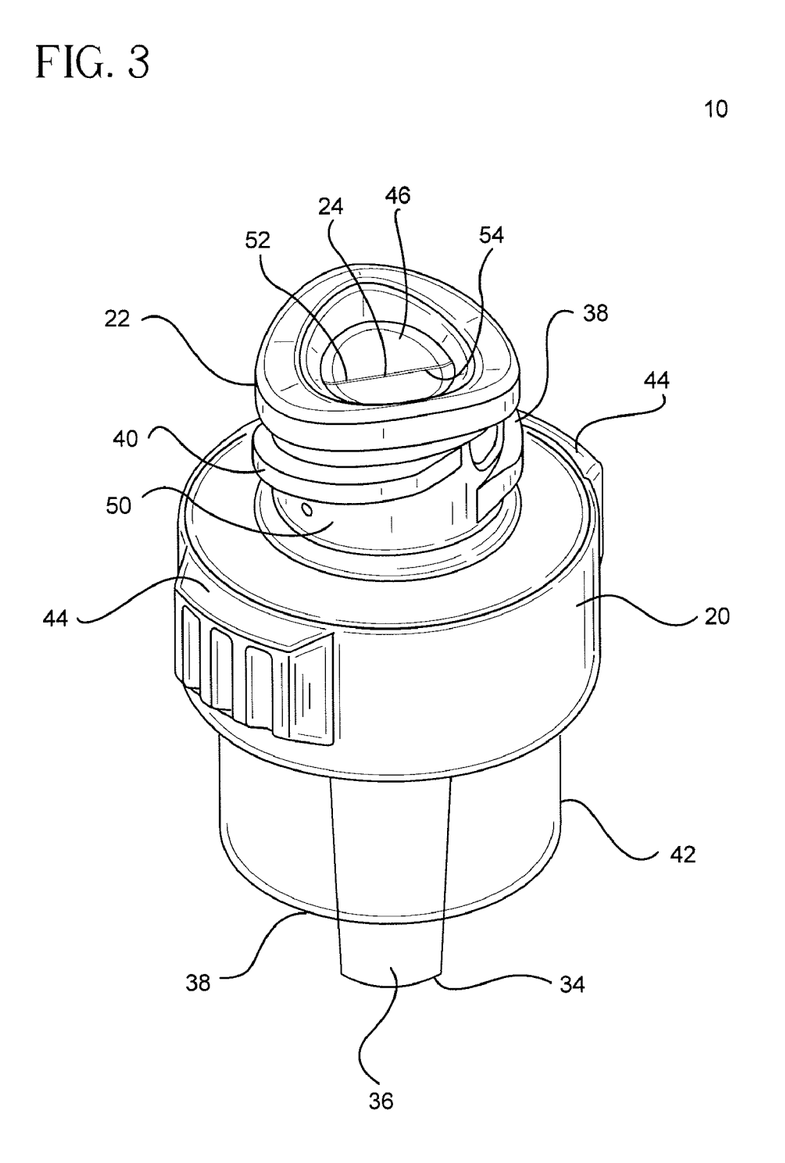
FIG. 3 is a perspective side view of a vascular access device.

The standard features of a vascular access device 10 are better illustrated in FIGS. 2 and 3. As illustrated in these Figures, the septum 22 includes a portion that extends beyond the body 20 but is otherwise disposed substantially within the body 20. The body 20 may include a cannula 34 for coupling with a catheter or other medical device. The cannula 34, along with other components of the body 20, may cooperate to form a lumen 36 through the body 20. The body 20 may also include connection regions 38, such as female Luer connector 40 or male Luer connector 42, to enable the vascular access device to be selectively coupled to other medical devices. Additionally, the body 20 may include grips 44, which may be ridges or other structures on the surface of the body 20, to facilitate the manipulation of the vascular access device 10. The body 20 may include other features or structures common to vascular access devices.

With continuing reference to FIGS. 2-5, the septum 22 is substantially disposed within the body 20 of the vascular access device 10. More specifically, the septum 22 includes a top disk 46, a bottom disk 48, and a throat region 50 extending between the top disk 46 and the bottom disk 48. The throat section 50 and bottom disk 46 are more clearly visible in the cross section view presented in FIGS. 4 and 5. As used herein, the top disk 46 may also be referred to as a saddle 46 and the bottom disk 48 may be referred to as an anchor 48. With more particular reference to FIG. 2, the septum 22 is shown to include a slit 24 having opposing slit surfaces 52, 54. As described above, the opposing slit surfaces 52, 54 of the slit 24 are moved apart to open the slit when the tip 30 of a medical device is inserted into a vascular access device 10.

Figure 4:
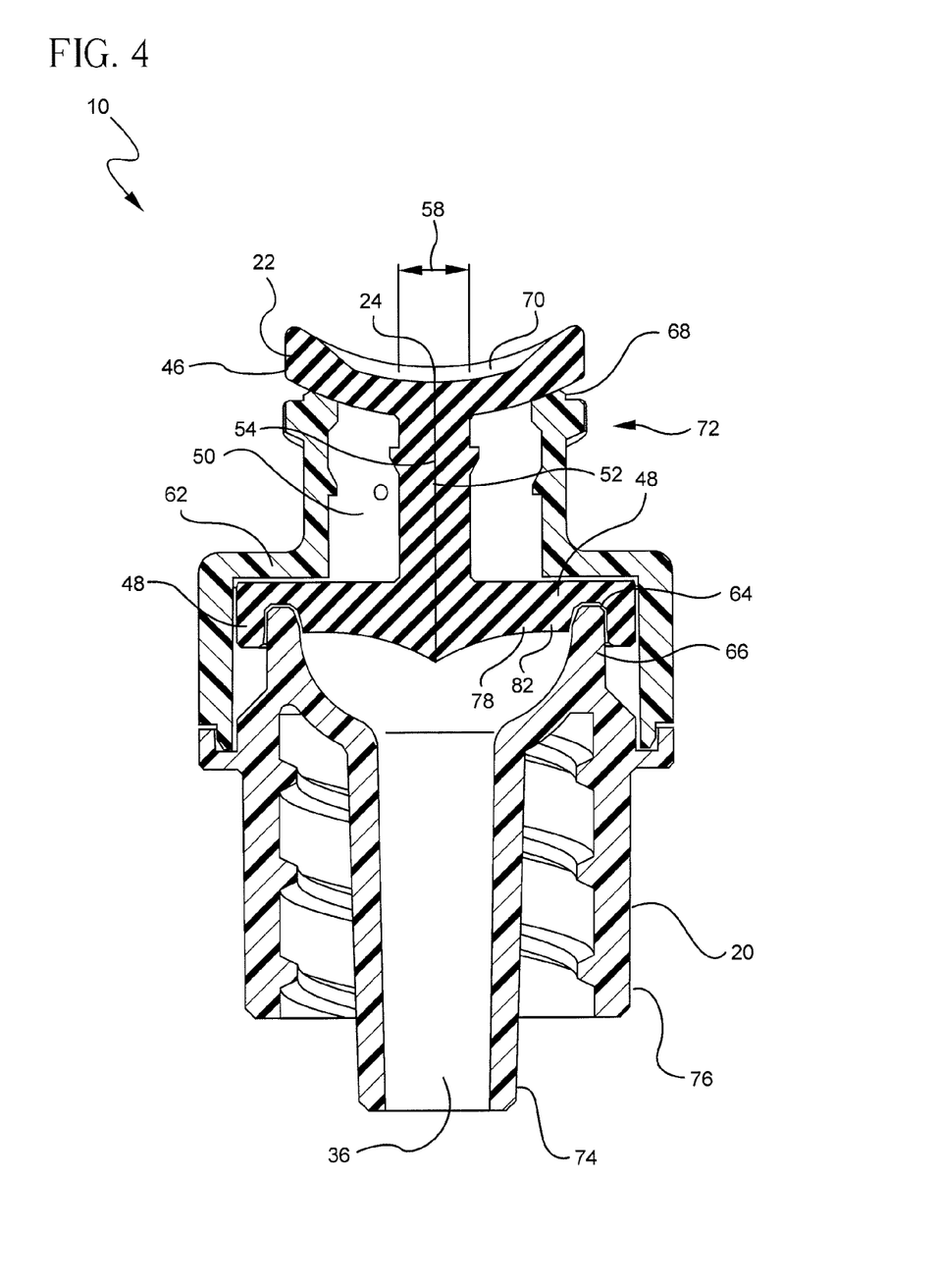
FIG. 4 is a cross section view of a vascular access device.
Figure 5:
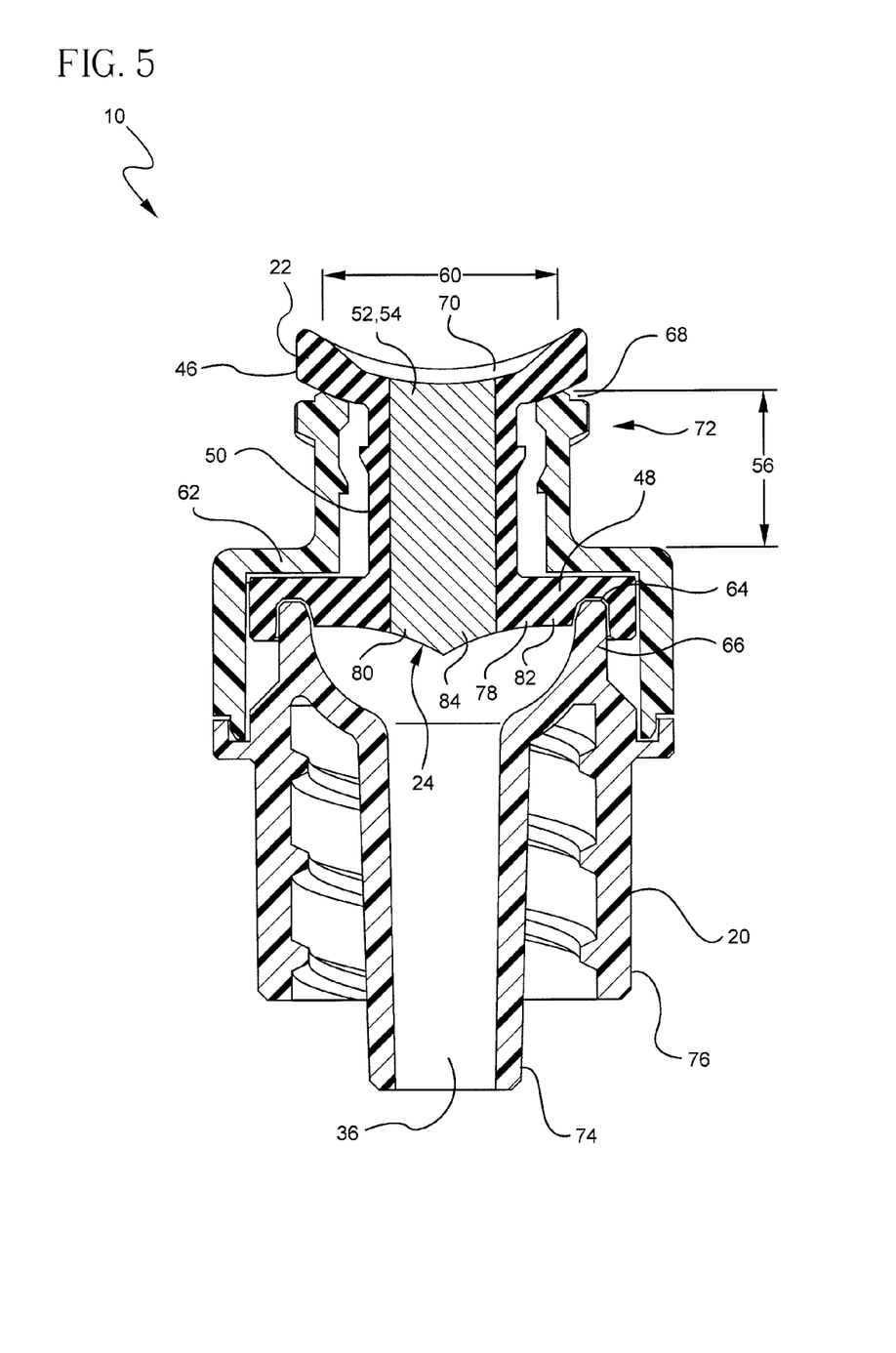
FIG. 5 is a cross section view of a vascular access device with the cross section being 90 degrees offset from the cross section of FIG. 4.

Referring now to FIGS. 4 and 5, cross sectional views of a vascular access device 10 are shown to better illustrate particular aspects of an exemplary septum 22. As illustrated, FIGS. 4 and 5 are cross sections of the same vascular access device with the cross sections being taken along orthogonal lines of cross section. FIG. 4 illustrates a vascular access device 10 showing the throat region 50 spanning between the saddle 46 and the anchor disk 48. The throat region 50 may have any suitable length 56 between the saddle 46 and the anchor 48, which length 56 may vary to accommodate the configuration of the body 20. As one example, the length 56 may be selected to position the anchor disk 48 within the body 20 and the saddle 46 outside the body, as illustrated.

The throat region 50 also has a thickness 58, shown in FIG. 4, and a width 60, shown in FIG. 5. The width 60 and thickness 58 of the throat region 50 may be selected to meet the needs of the medical practitioner and the vascular access device 10 in which the septum 22 is being incorporated. The width 60 may be selected to provide sufficient room for a slit 24 sufficiently wide to accommodate the desired tips 30 of the cooperating medical devices 26. The thickness 58 of the throat region 50 may be selected to provide sufficient strength to the throat region while still providing sufficient elasticity and/or flexibility to allow the slit surfaces 52, 54 to separate as the tips 30 are inserted into the vascular access device 10.

The bottom disk 48, or anchor disk, may be configured to have a size, such as a diameter, that is selected to fit within the body 20 and to be retained in the body by a shoulder region 62. Additionally or alternatively, the bottom disk 48 may be anchored within the body 20 through other means, such as through adhesives or fasteners. As illustrated in FIGS. 4 and 5, the bottom disk 48 may include one or more grooves or slots 64 that may be adapted to cooperate with portions of the body 20 to further anchor the septum 22 in place. The bottom disk 48 and one or more portions of the body 20 may be configured to anchor the septum 22 rotationally within the body, longitudinally within the body, and/or laterally within the body. As one example, fingers 66 of the body 20 may be adapted to fit in the grooves 64 to prevent lateral movement and/or rotational movement of the septum 22. Additionally or alternatively, the fingers 66 may be sized to press the bottom disk 48 into the shoulder region 62 so that the top surface of the bottom disk is in contact with the body 20. As one example, the fingers 66 may cause the bottom disk 48 and the body 20 to form a seal. In addition to the features described, the bottom disk 48 may include additional features or elements customary for vascular access devices.

FIGS. 4 and 5 illustrate that the top disk 46 may be configured to be disposed outside of the body 20. As illustrated the bottom surface of the top disk 46 rests on the upper end 68 of the body 20. FIG. 4 further illustrates that the top disk 46 may be configured to provide a well 70 or indentation. The well 70 may assist in guiding the tip 30 of the cooperating medical device 26 into the slit 24 of the vascular access device 10. As seen in FIGS. 4 and 5, the well 70, in some implementations, may cause the top disk 46 to resemble a saddle. The well 70, when present, may be formed by thinning a portion of the top disk 46 and/or by applying upward pressure to the outside edge of the top disk 46. As one example, the septum 22 may be configured with a throat region 50 that is minimally shorter than the distance between the shoulder region 62 of the body 20 and the upper end 68 of the body. Accordingly, the septum material of the throat region 50 and the top disk 46 may be slightly stretched by this difference causing the top disk to flex forming the well 70. The well 70 may be formed in other suitable manners.

As discussed above and as illustrated in FIG. 4, the top disk 46 contacts the upper end 68 of the body 20. The interface between the top disk 46 and the upper end 68 of the body 20 may form an additional seal, which may be similar to the seal between the bottom disk 48 and the body 20. Additionally or alternatively, an adhesive may be used to bond the top disk 46 to the upper end 68 of the body. Moreover, structural features, such as grooves, may be incorporated into the bottom surface of the top disk 46 to cooperate with the body 20 to form a seal. The seals formed by the top disk 46 and/or the bottom disk 48 and the body 20 are adapted to seal, or at least substantially seal the lumen 36 through the body 20. Moreover, when the slit surfaces 52, 54 are together (i.e., not separated by a tip 30 and not otherwise separated by tears, cracks, or other modifications to the septum), the septum 22 seals, or at least substantially seals the passage through the lumen of the body 20.

For purposes of description, the upper end 68 of the body 20 and the portions adjacent thereto may be referred to as a first body end region 72 whereas the lower end 74 of the body 20 and the portions adjacent thereto may be referred to as the second body end region 76. The use of the terms first and second to denominate the end regions, or other elements described herein, is not meant to imply any order between the two end regions but merely to distinguish between the two. While the terms top and bottom are also used herein to designate and distinguish features, components, or parts of the vascular access device, it should be understood that the orientation of the vascular access device may change during use of the device; accordingly, the terms top and bottom are not intended to be limiting with respect to orientation during use of the device but are referencing relative locations in the Figure being discussed.

The body 20 and the septum 22 may be constructed of a variety of suitable materials. Commonly, the body 20 of the vascular access device 10 will be made of a plastic, and preferably a plastic material that facilitates molding the body. As illustrated in FIGS. 4 and 5, the body 20 is formed from two pieces that are molded or adhered together to form the body once the septum 22 is in place. Other methods and materials may be used for manufacturing the body 20, some of which may be currently practiced and some of which may be developed in the future.

Similarly, the septum 22 may be made of a variety of suitable materials and through a variety of suitable manufacturing methods. For example, the septum may be formed from liquid silicone rubber through suitable molding procedures, such as insert molding, injection molding, other molding techniques, or a combination of molding techniques. The septa 22 of the present disclosure are perhaps best described as comprising at least two materials. The two materials that form the septum 22 may be distinct materials used to form different portions of the septum or the materials may be integrally related so as to be indiscernible by the average user. For the purposes of the present discussion, the septa 22 will be described as comprising at least a first material and a second material, at least one of which is adapted to resist tearing of the septum 22. Additionally or alternatively, the septa 22 may include additional materials, which may be denominated as third, fourth, etc. materials, that may, or may not, impart tear-resistant properties. Some examples of such combinations will be described herein, while others are within the scope of the present disclosure.

The base material of the septa 22, which may be referred to as the first material, may be or include any suitable material. Common examples of suitable materials include, but are not limited to, liquid silicone rubber, high consistency rubber, and polyisoprene rubber. The base material may be selected based on a variety of factors, such as compatibility with the body 20, compatibility with the cooperating devices 26 that will be used with the vascular access device 10, and/or compatibility with any other materials that may be incorporated into the septum 22 or other parts of the vascular access device.

Additionally or alternatively, the base material may be selected to provide the base material with certain properties that may be desirable for septa of vascular access devices. As one exemplary but non-limiting example of such a property, the base material may be selected to provide the septa with high tear strength, such as greater than or equal to 260 ppi. Additionally or alternatively, the material may be selected to provide the septa, or particular regions of the septa, with high elongation tolerance, such as greater than or equal to 350% elongation before breaking. Additionally or alternatively, the materials considered to be the base materials may be selected or configured to provide high tensile strength to the septum, or particular regions thereof, such as greater than or equal to 1000 pounds per square inch. Still additionally or alternatively, the base material of the septa may be selected and/or prepared to provide the septa with low compression set percentage, such as less than or equal to 20% following compression at 70° C. for 22 hours. As yet another exemplary and non-limiting example of properties that may be desirable in septa base material, the septa may be formed and/or configured to provide one or more regions of the septa with a hardness number between 20 and 60 on the Shore A hardness scale. The base material of the septa 22 may be selected to provide one or more of these properties or other properties.

Depending on the properties provided by the base material, the septa's dependence on the second material to provide tear-resistance properties to the septa may be reduced. For example, the base material may provide tear-resistance properties to the septa such that the second material may be needed only as a backup, or under extreme use conditions. In some implementations of the present disclosure, the base material may be selected to provide sufficient tear-resistance properties to the base material to enable the manufacture of septa having tear-resistance properties while only using the base material, in which case the second material of the septa may be an adhesive, sealant, colorant, or other material that does not significantly contribute to the tear-resistance properties of the septa. Additionally or alternatively, the septa 22 may be formed from a composite base material that renders distinguishing between the first and second material difficult and also provides the septa with the tear-resistance properties within the scope of the present disclosure.

Returning to the schematic representations of a vascular access device 10 shown in FIGS. 4 and 5, a septum 22 comprising a first material 78 and a second material 80 is illustrated showing a first material that is a base material 82 and a second material that is a lubricating material 84. The septum 22, and particularly the regions adjacent the slit 24, is under stress, which may be from a number of directions, when the vascular access device 10 is coupled to cooperating medical devices 26 by inserting the tip 30 of the other device 26 into the slit 24. Some or all of these stresses may be reduced by lubricating the surfaces that contact the cooperating medical device, such as the top surface of the top disk and the slit surfaces. The lubricating second material 84 may be selectively disposed on the septum 22 adjacent to the slit 24. As one example, the lubricating material 84 may be disposed on one or more of the slit surfaces 52, 54. Additionally or alternatively, the lubricating material 84 may be disposed primarily on the top surface of the top disk 46, such as in the well 70, to be in contact with the tip 30 as it first contacts the septum 22. The lubricating material 84 may be disposed on both the top disk top surface and on the slit surfaces. Additionally or alternatively, the lubricating material 84 initially may be disposed on one or more of the septum surfaces and may be spread to the other surfaces during use of the vascular access device 10.

The lubricating material 84 may be selected from among the presently known and yet to be developed lubricants. The lubricant may be selected for its lubricity under the expected operating conditions. Additionally or alternatively, the lubricant may be selected for the durability of the lubricity after repeated uses of the vascular access device 10. Additionally or alternatively, the lubricant may be selected for the strength and/or durability of the adhesion between the lubricant material and the septum base material, such as when the lubricating material 84 is a coating material. Additionally or alternatively, the lubricant may be selected for its absorption rate into silicone rubber to promote the maintenance of the lubricant on the surface of the septum 22 rather than absorbed into the material of the septum. And still additionally or alternatively, the lubricant may be selected based on economic factors such as manufacturing costs, time, or complexity. While a variety of suitable lubricants are within the scope of the present disclosure, the features and benefits of particular lubricants are disclosed below as non-limiting examples.

The lubricating material 84 that may be used to provide a tear-resistant property to the septa 22 within the scope of the present disclosure may include a parylene coating. Parylene coatings may provide the benefit of high and durable lubricity and, additionally or alternatively, may provide the benefit of good adhesion between the parylene and the silicone rubber that may be used as a base material for the septum. Parylene may also be beneficial for its low permeability to moisture and gas and/or for its bacterial resistance properties. A variety of parylene coating materials are known, such as parylene C, parylene N, parylene D, and parylene HT, any of which may be advantageously used as the lubricating material 84. Depending on the intended use of the vascular access device 10, parylene C, N, or HT may be preferred. The parylene coating may be applied in any suitable thickness. Depending on the configuration of the vascular access device 10, it is presently believed that the parylene coating may be as thin as a 1 μm. In most vascular access devices presently contemplated, the parylene coating will generally be sufficiently thick without being any thicker than about 5 μm. However, the parylene coating may be applied to whatever thickness might be suitable or desirable based on factors such as the configuration of the vascular access device 10, the intended use of the vascular access device 10, or other factors.

Another suitable lubricating material 84 that may be used in septa 22 according to the present disclosure to reduce the stress on the septa and resist tearing of the septa may include fluorinated silicone oil. Fluorinated silicone oil may provide many benefits to the septa 22 of the present disclosure. As a non-limiting exemplary benefit that may be provided by the use of fluorinated silicone oil, the use of fluorinated silicone oil may reduce the absorption of the silicone oil into the silicone rubber of the septum 22. The reduced absorption of the fluorinated silicone oil may result in the lubricating silicone oil remaining on the slit surface and/or septum top surface for a longer period of time allowing better performance and longer life.

One exemplary fluorinated silicone oil may include trifluoropropyl methyl siloxane. The fluorinated silicone oil may be applied as substantially pure fluorinated silicone oil. Additionally or alternatively, a copolymer may be used, such as a copolymer of trifluoropropyl methyl siloxane and dimethyl siloxane. Additionally or alternatively, a copolymer may be formed between a fluorinated silicone and hydrocarbon or silicone lubricant oil. Whether substantially pure fluorinated silicone oil, such as 100% trifluoropropyl methyl siloxane, or a copolymer of fluorinated silicone oil is used, the lubricant may be provided in any suitable density. In the context of the present vascular access devices, it is presently believed that a density of less than or equal to about 125,000 cps is suitable. When the fluorinated silicone oil is an oil of 100% trifluoropropyl methyl siloxane, the weight density may be about 350 cps.

The amount of fluorinated silicone oil appropriate or suitable for sufficiently lubricating the septum 22 may vary depending on the configuration of the vascular access device 10, the materials chosen for the septum 22, and the intended use of the vascular access device 10. However, as little as 0.23 mg of fluorinated silicone oil may be used per septum 22. It is presently believed that use of at least 0.68 mg of fluorinated silicone oil may be desirable for some configurations and applications of the vascular access devices of the present disclosure.

With continuing reference to FIG. 5 and the continuing discussion of lubricating materials 84 as part of the septa 22 to provide tear-resistant properties to the septa, the foregoing discussion illustrates that a variety of lubricating coating materials may be applied to the septa 22 within the scope of the present disclosure. Additionally or alternatively, the lubricating material 84 of the present disclosure may be a curable lubricating material 84. For example, a curable liquid may be applied to the septa 22, such as on the top disk 46, into the slit 24, or both, and then heat or UV cured. Once cured, the liquid coating will remain in place and provide durable lubrication. A variety of lubricious curable liquids may be used that would provide sufficient lubrication and be economically curable.

As one, non-limiting example of a curable liquid that may be applied to provide the lubricating, tear-resistant properties, a lubricious liquid silicone rubber may be placed on the top surface or in the slit 24 of the septum 22 and cured in place. A lubricious, or self-lubricating, silicone rubber is one that has more uncured, cyclic or linear silicone molecules inside the cured matrix. Therefore, in some implementations of this exemplary embodiment, the septa 22 will be formed of the base material 82 and cured. The lubricating material 84 then may be added in the form of a liquid silicone, which is subsequently cured in a manner that will preserve sufficient uncured silicone molecules in the cured matrix to provide the self-lubricating properties. Due to the high-compatibility with the silicone rubber, the uncured silicone oil will stay through the rubber matrix, which will provide durable lubricity over repeated uses of the septum 22. While the use of a lubricious, liquid silicone-silicone rubber coating is one example of a curable lubricating material that may be applied, other suitable materials may be used, one or more of which may be applied or implemented in different manners suitable for the selected material.

Figure 6:
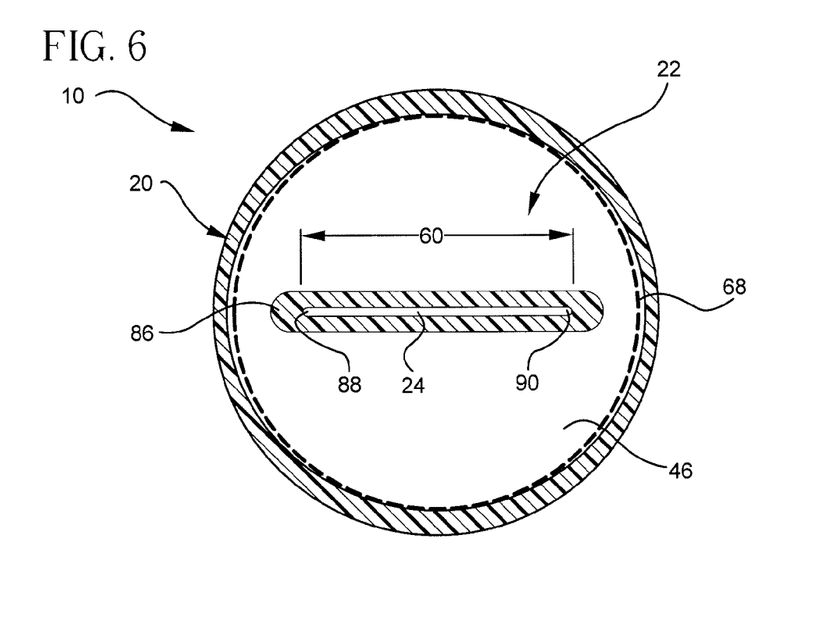
FIG. 6 is a top view of a vascular access device including an elastomeric material.

Referring now to FIG. 6, a somewhat schematic top view of a vascular access device 10 is illustrated. FIG. 6 illustrates the outer region of the body 20 and the top surface of the top disk 46 of the septum 22. FIG. 6 further illustrates the slight overlap of the top disk 46 over the upper end 68 of the body 22. In most respects, the vascular access device 10 shown in FIG. 6 is substantially the same as the vascular access devices described above. For example, the size, configuration, and function of the septum 22 and body 20 may be substantially the same. In the interest of brevity, only the aspects of FIG. 6 that differ from the preceding discussion will be described in connection with FIG. 6.

In the vascular access device 10 of FIG. 6, the septum 22 is provided with a second material that includes an elastomeric material 86 disposed around the slit 24. The elastomeric material 86 may be disposed completely around the slit 24 or adjacent to particular portions of the slit 24, such as adjacent to one or both of the first slit end 88 and the second slit end 90 located at the ends of the slit width 60. As before, the terms first and second are used merely to distinguish between the distinct ends without the implication or requirement that one end comes before or after the other in any way. As illustrated, the elastomeric material 86 is disposed immediately adjacent to the slit 24 and may form at least part of the slit surfaces 52, 54. Additionally or alternatively, the elastomeric material 86 may be offset from the slit 24 by another material that forms the slit surfaces. For example, a curable, lubricious coating may be applied to the elastomeric material 86 to form the slit surfaces 52, 54. Additionally or alternatively, the elastomeric material 86 may be insert molded into the septum 22 to be disposed in the top disk 46 and/or the throat 50 or other regions of the septum 22. Regardless of how the elastomeric material 86 is incorporated into the septa of the present disclosure, the elastomeric material will be operatively associated with the slit 24 to facilitate the selective expansion and contraction of the slit.

As used herein, the elastomeric material 86 that may be incorporated in the septa 22 to provide tear-resistant properties to the septa refers to any material that has a higher modulus of elasticity than the base material of the septa. A suitable elastomeric material 86 would have properties to facilitate its economic incorporation into the septa, such as relatively low supply costs and relatively high compatibility with the other materials of the septa. Additionally or alternatively, a suitable elastomeric material 86 may be selected for its biomedical properties, such as resistance to bacterial growth, stability under the conditions of use, etc. Polyurethane foam is one example of a suitable elastomeric material within the scope of the present disclosure. Other suitable elastomeric materials may include materials that are highly porous and compressible. Several foam elastomers are available that are suitable for the present implementations and are within the scope of the present disclosure.

Figure 7:
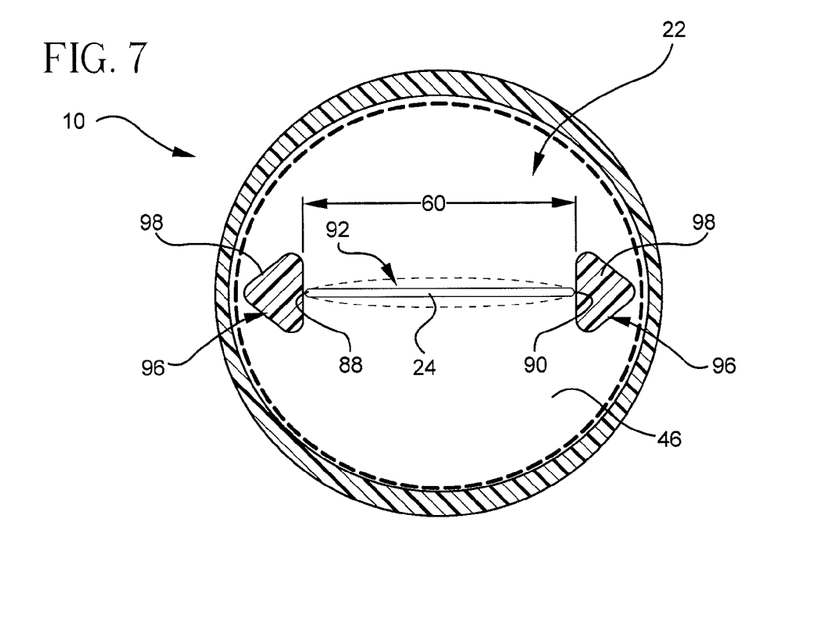
FIG. 7 is a top view of a vascular access device including a slit stop.
Figure 8:
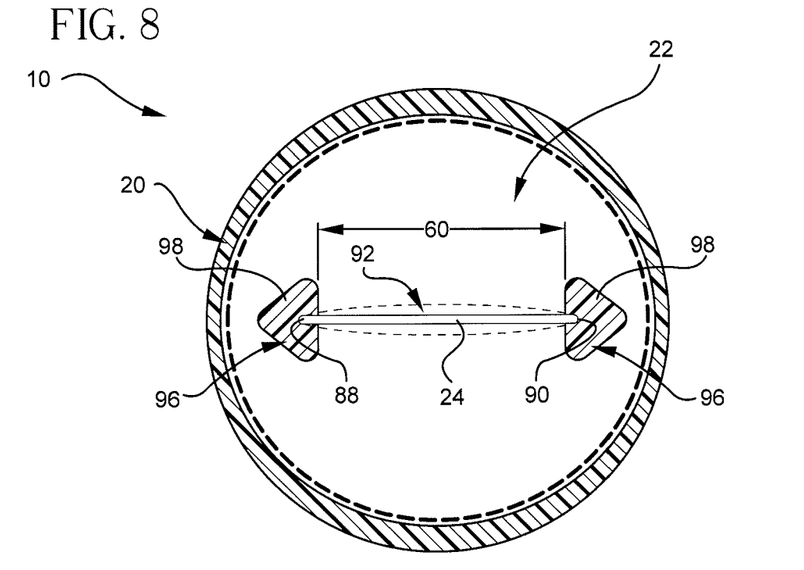
FIG. 8 is a top view of a vascular access device including a slit stop.
Figure 9:
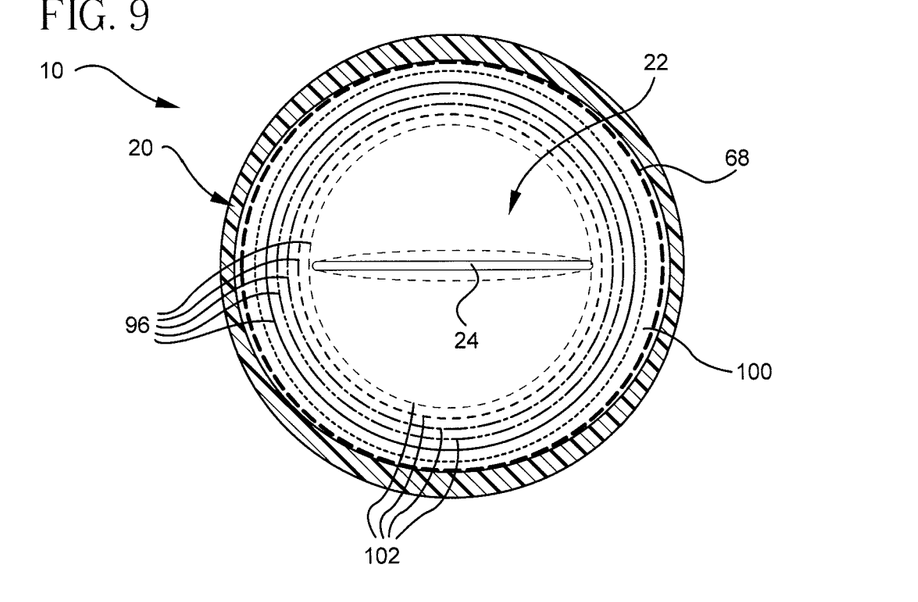
FIG. 9 is a top view of a vascular access device including a slit stop.

Referring now to FIGS. 7-9 collectively, a top view of vascular access devices 10 are schematically illustrated in a manner similar to the representation in FIG. 6, where common elements are identified by the same reference numbers. As in FIG. 6, the top disk 46 of the septum 22 is illustrated in FIGS. 7-9 to show, in schematic form, the first and second slit ends 88, 90 separated by the slit width 60. FIGS. 7-9 additionally illustrate, through the use of dotted lines representing an open slit 92, a schematic representation of what happens to the slit 24 when the septum 22 is opened by the tip 30 of a cooperating medical device 26.

FIGS. 7-9 further illustrate a septum 22 having at least one slit stop 96 disposed substantially adjacent to the first and second slit ends 88, 90. Septa 22 within the scope of the present disclosure may include one or more slit stops 96, which may be disposed in operative association with at least one of the slit ends 88, 90. In some implementations, it may be preferred to position at least one slit stop 96 adjacent to, or at least near, the slit ends 88, 90 where the septa 22 may be expected to experience the greatest stress during use. As illustrated in FIG. 8, a slit stop 96 that surrounds the slit end may provide tear resistance against both radial tears and circumferential tears emanating from the slit end. In other implementations, it may be preferred to provide a lubricating material 84 layer between the slit ends 88, 90 and the slit stop 96 or to provide another material layer between the slit ends 88, 90 and the slit stop 96.

The slit stops 96 may have a depth extending in the longitudinal direction of the septum 22 (i.e., in the direction between the top disk and the bottom disk aligned with the longitudinal axis of the throat region), which depth may be only a few millimeters or as long as the septum 22 itself. For example, the slit stops 96 may extend only a short distance into the top disk 46, may extend all the way through the top disk, may extend part way or completely through the throat region 50, and/or may extend partially or completely through the bottom disk 48. The depth of the slit stops 96 may vary depending on one or more of: the configuration of the slit stops, examples of which are illustrated in FIGS. 7-9; the materials used in the slit stops 96; the configuration of the septum 22, the slit 24, and/or the body 20; and/or the intended uses of the vascular access device 10.

The slit stops 96 may be formed of any suitable material that is more tear resistant than the remaining material of the septa 22. Generally, the base material 82 of the septa 22 requires some flexibility and pliability to seal the lumen 36 of the body 20 and to suitably seal around the tip 30 of the cooperating medical devices 26. The material of the slit stops 96 may be a harder and/or stronger material. Additionally or alternatively, the material of the slit stops 96 may be configured to resist tearing based on the alignment of the molecules in the matrix and/or based on the alignment of fibers within the matrix. The material of the slit stops 96 may be selected based upon a variety of factors, such as one or more of those factors discussed elsewhere herein. The material of the slit stops 96 may be molded and cured and then used in an insertion molding process to be disposed in the desired location within the septa 22. Additionally or alternatively, the slit stops 96 may be partially or completely co-molded along with the remainder of the septum 22. Additionally or alternatively, the septa 22 may be formed followed by molding the slit stop 96 around, on, or in the previously formed septa 22, such as via an insertion molding process. The methods used to manufacture septa 22 having one or more slit stops 96 may vary depending on the configuration of the slit stops, the configuration of the septa 22 generally, and/or any combination of the other factors discussed herein that may allow a manufacturer to customize a vascular access device 10 within the scope of the present disclosure.

Referring now more specifically to FIGS. 7 and 8, the slit stops 96 are represented as triangular bumpers 98. The bumpers 98 may be in any suitable shape or configuration. FIG. 7 illustrates the slit stops 96 disposed slightly offset from the slit ends 88, 90. FIG. 8 illustrates the slit stops 96 disposed in the septum 22 such that the slit 24 extends into the slit stops 96. As described above, the configuration in FIG. 8 may provide tear resistance against the radial stresses and against the circumferential stress that may be applied to the slit ends. Septa 22 having bumpers 98 as the slit stops 96 may be conveniently formed via insertion molding techniques. Bumpers 98 are one example of a slit stop 96 that may extend as deep into the septa 22 as desired to resist tearing. In some examples, the configuration of the bumper 98 may vary along the length of the septa 22, such as changing cross-sectional shape from the top disk 46 to the throat region 50, should the bumper 98 extend that far down the septa 22.

Referring now to FIG. 9, the slit stop 96 is illustrated somewhat schematically as an outer ring 100. The outer ring 100 may be similar in many respects to the slit stops 96 described above, including the bumpers 98. For example, the outer ring 100 may include material that is harder and/or stronger than the remaining material of the septum 22. Additionally, however, the outer ring 100 includes fibers 102 that are aligned circumferentially around the outer ring 100, as schematically illustrated. Additionally or alternatively, the outer ring 100 may include nanofibers and/or nanoparticles that are substantially aligned circumferentially around the outer ring 100. As used herein, the term fibers 102 will be used to refer generally to fibers or particles, whether nano-sized or not, that are incorporated into the outer ring 100. The aligned fibers 102 may act as a barrier to propagation of a tear from the slit 24. As described above and illustrated in FIG. 9, the outer ring 100 and the slit 24 may be associated such that the slit ends 88, 90 are disposed adjacent to the outer ring 100. Additionally or alternatively, one or both of the slit ends 88, 90 may be disposed within the outer ring 100.

The fibers 102 of the outer ring 100 may include fibers of any suitable material. Suitable materials will be compatible with the material selected for the outer ring 100. The outer ring 100 may include materials similar to the materials of the bumper-style slit stops 98. Additionally or alternatively, the outer ring 100 may be formed of silicon rubber or other suitable material for the remainder of the septum 22. As illustrated, the fibers 102 are aligned circumferentially around the outer ring 100. The fibers 102 may be aligned by the flow of the silicon rubber during the formation of the outer ring 100. For example, the septum 22 may be formed from a first molding process followed by a second molding process during which the outer ring is formed and the fibers are aligned by the manner of the molding process.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Where the disclosure, the presently filed claims, or subsequently filed claims recite "a" or "a first" element or the equivalent thereof, it should be within the scope of the present inventions that such disclosure or claims may be understood to include incorporation of one or more such elements, neither requiring nor excluding two or more such elements.

Applicants submit claims herewith and reserve the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:

1. A vascular access device, comprising:
a body defining a lumen extending therethrough;
a septum at least partially disposed in the body to at least substantially seal the lumen extending through the body;
a slit formed through the septum, the slit having a width between a slit first end and a slit second end; and
at least one slit stop to resist tearing of the septum, the slit stop being disposed at least in the top of the septum and at least substantially adjacent to at least one of the slit first and second ends, the septum comprising a first material and the slit stop comprises a second material.

2. The vascular access device of claim 1, wherein the at least one slit stop includes a bumper.

3. The vascular access device of claim 1, wherein the at least one slit stop includes an outer ring.

4. The vascular access device of claim 3, wherein the outer ring includes aligned fibers.

5. The vascular access device of claim 1, further comprising a lubricating material.

6. The vascular access device of claim 5, wherein the lubricating material is selected from a parylene coating, a silicone oil coating, and a fluorinated silicone oil coating.

7. The vascular access device of claim 5, wherein the lubricating material is disposed at least in a portion of the slit.

8. The vascular access device of claim 5, wherein the lubricating material is a curable, lubricating material.

9. The vascular access device of claim 1, wherein the second material is an elastomeric material.

10. The vascular access device of claim 9, wherein the second material includes a highly porous material.

11. The vascular access device of claim 1, wherein the slit stop is disposed substantially within the septum.

12. The vascular access device of claim 1, wherein the second material is disposed within the first material.

13. The vascular access device of claim 12, wherein the outer ring includes aligned fibers.

14. A vascular access device, comprising:
a body means for selective coupling to a vascular system of a patient and to at least one additional medical device and having a passage extending therethrough;
a sealing means including a slit for selectively and at least substantially sealing the passage through the body, wherein the slit has a slit width between a slit first end and a slit second end; and
a slit stop for discouraging tearing of the sealing means disposed at least in the top of the sealing means and at least substantially adjacent to the first and second ends of the slit, wherein the sealing means comprises a first material and the slit stop comprises a second material.

15. The vascular access device of claim 14, further comprising a lubricating means for reducing friction in the slit disposed at least substantially adjacent to at least a portion of the slit.

16. The vascular access device of claim 14, wherein the means for discouraging tearing includes a barrier means for impeding the propagation of tears disposed at least substantially adjacent to at least a portion of the slit.

17. The vascular access device of claim 14, wherein the means for discouraging tearing includes an elastic means for increasing the flexibility of the seal means disposed at least substantially adjacent to at least a portion of the slit.

18. The vascular access device of claim 14, wherein the means for discouraging tearing of the sealing means includes a bumper.

19. The vascular access device of claim 14, wherein the means for discouraging tearing of the sealing means includes an outer ring.

20. A vascular access device, comprising:
a body defining a lumen extending therethrough;
a septum at least partially disposed in the body to at least substantially seal the lumen extending through the body;
a slit formed through the septum, the slit having a width between a slit first end and a slit second end; and
at least one slit stop disposed at least substantially adjacent to at least one of the slit first and second ends, and wherein the septum comprises a first elastomeric material and the slit stop comprises a second elastomeric material.

* * * * *